United States Patent [19]

Manderino et al.

[11] Patent Number: 4,515,890
[45] Date of Patent: May 7, 1985

[54] IMMUNOASSAY OF TERMINAL DEOXYNUCLEOTIDYL TRANSFERASE

[75] Inventors: George L. Manderino, Gurnee; Adoracion F. Suarez, Chicago, both of Ill.

[73] Assignee: Abbott Laboratories, North Chicago, Ill.

[21] Appl. No.: 440,129

[22] Filed: Nov. 8, 1982

[51] Int. Cl.³ .................. C12Q 1/66; G01N 33/54; G01N 33/58
[52] U.S. Cl. .................................. 435/7; 436/531; 436/534; 436/535; 436/813
[58] Field of Search .................. 435/7; 436/531, 534, 436/535, 813

[56] References Cited

U.S. PATENT DOCUMENTS

| 3,839,153 | 10/1974 | Schuurs et al. | 436/531 |
| 3,932,141 | 1/1976 | Beall et al. | 436/531 |
| 4,020,151 | 4/1977 | Bolz et al. | 436/531 |
| 4,307,189 | 12/1981 | Kit | 435/7 |
| 4,363,634 | 12/1982 | Schall, Jr. | 435/7 |

FOREIGN PATENT DOCUMENTS 0118671  9/1981  Japan ........................ 435/7

OTHER PUBLICATIONS

Coleman, Archives of Biochemistry and Biophysics, vol. 182, pp. 525–532, 1977.
Bollum et al., Methods in Enzymology, vol. XXIX, 1974, pp. 70–80.
Cibull et al., American Journal of Clinical Pathology, vol. 77(4), 1982, pp. 420–433.
Deibel et al., Journal of Clinical Investigation, vol. 67, Mar. 1981, pp. 725–734.
Janossy et al., Journal of Immunology, vol. 123, No. 4, Oct. 1979, pp. 1525–1529.
Chirpich, Biochimica et Biophysica Acta, 518, 1978, pp. 535–538.
Siddiqui, Biochimica et Biophysica Acta, 745, (1983), 154–161.
Ashley, Virology, vol. 77, 1977, pp. 367–375.

Primary Examiner—Sam Rosen
Assistant Examiner—William J. Herald
Attorney, Agent, or Firm—M. M. O'Brien; D. K. Shelton; M. L. Katz

[57] ABSTRACT

This disclosure relates to a method for the quantitative in vitro determination of terminal deoxynucleotidyl transferase in human blood extracts, bone marrow extracts and lymphocyte extracts and wherein the terminal deoxynucleotidyl transferase is extracted with an extractant containing a nonionic surfactant, an anticoagulant and a reducing agent.

10 Claims, No Drawings

IMMUNOASSAY OF TERMINAL DEOXYNUCLEOTIDYL TRANSFERASE

BACKGROUND OF THE INVENTION

Terminal deoxynucleotidyl transferase (TdT) is a DNA polymerase which adds deoxyribonucleotide monophosphate to DNA in the absence of a template. TdT is a normal constituent of a subpopulation of immature lymphocytes in the hematopoietic system. TdT is normally expressed in approximately 65% of thymocytes and 1-5% of bone marrow cells yet is virtually absent in circulating lymphocytes. Bollum, *J. Biol. Chem.*, 235:2399 (1960), Coleman, et al, *Proc. Natl. Acad. Sci., U.S.A.*, 71:4404 (1974). As such, TdT is regarded as a biochemical marker for certain immature lymphocytes.

Elevated TdT levels have been reported in the circulation of severely malnourished children. Chandra, et al, *Acta. Pediatr. Scand.*, 68:841 (1979). The rise of TdT levels in these individuals correlates with an increase in levels of immature (null) lymphocytes suggesting that severe nutritional deprivation might retard normal lymphocyte maturation.

Elevated TdT levels have also been described in blood and bone marrow cells of the majority of patients with acute lymphoblastic leukemia. McCaffrey, et al, *Proc. Natl. Acad. Sci., U.S.A.*, 70:521 (1973); Coleman, et al., *Cancer Research*, 36:120, (1976). In this disease the blast cells have many of the morphological, histochemical, and surface membrane characteristics of immature lymphocytes. Brandt, et al, Cancer, 42:817 (1978); Cressells, et all, *Lancet*, 2:1307, (1977); Diekel, et al., *J. Clin. Invest.*, 67:725 (1981). In contrast, blasts from patients with acute myelogenous leukemia have only sporadically been reported to contain detectable levels of TdT. Gordon, et al., *Blood*, 52:1079, (1978); Srivastaya, et al., *Cancer Research*, 36:3847 (1976).

Conventional techniques for measuring TdT enzymatic activity rely upon a radiopolymerization procedure referred to as a terminal deoxynecleotidyl transferase DNA-polymerization assay. Such TdT DNA-polymerization assays measure the enzymatic activity of TdT, i.e., the ability of TdT to add radiolabeled nucleotide triphosphates to a DNA template, and such assays are limited to measuring TdT enzymatic activity in lymphocyte extracts only.

In addition, it has been reported that TdT enzyme activity is substantially reduced if proper extraction procedures are not employed. Coleman, *Archives of Biochemistry and Biophysics*, 182, 525-532 (1977) has disclosed that a high salt concentration was mandatory for complete enzyme extraction. Coleman further noted that a buffer containing Tris (pH 7.7), EDTA, 1-mercaptoethanol and 0.5% Triton X-100 was an unsatisfactory extract to preserve TdT enzymatic activity.

It is an object of the present invention to provide a method for the quantitive determination of TdT. In addition, it is an object of the present invention to provide a method for quantitively determining TdT in human blood samples as well as samples obtained from bone marrow extracts and lymphocyte extracts. It is a further object of the present invention to provide a method for extracting TdT from a blood sample wherein antigenic activity of TdT is maintained.

SUMMARY OF THE INVENTION

The present invention relates to a solid phase "sandwich" immunoassay for quantitatively determining TdT antigen in a sample. A solid support coated with an antibody specific for TdT antigen is incubated with a sample suspected of containing TdT antigen to form an antibody-antigen complex on the solid support. Unbound material is removed and the complex on the solid support is treated with an anti-TdT, to form an antibody-antigen-anti-TdT complex on the solid support. The amount of anti-TdT bound to the antibody-antigen complex is measured as an indication of the amount of TdT antigen present in the sample.

In addition, if the sample to be assayed is a blood sample, the TdT antigen is extracted from the blood sample by treating the sample with a composition comprising a nonionic surfactant, anti-coagulant and a reducing agent in a buffered medium.

DETAILED DESCRIPTION OF THE INVENTION

The present invention relates to an immunoassay technique for measuring the concentration of TdT protein, in particular TdT antigen. According to a preferred embodiment of the present invention a blood sample specimen suspected of containing TdT antigen is treated with an effective amount of an extractant composition comprising a nonionic surfactant, anticoagulant and reducing agent in a buffered medium. The resulting extract mixture is stirred and centrifuged for a sufficient period of time to permit essentially all of the TdT antigen in the sample to be extracted into the supernatant. In order to increase recovery of TdT antigen, it is preferred that the sample is frozen and then thawed once prior to treatment of the sample with the extractant composition. Following the extraction procedure, the extracted sample containing TdT antigen is brought into contact with a TdT antibody, specific for TdT antigen in the sample, coated on a solid support. The resulting mixture is incubated for a sufficient period of time to permit formation of an antibody-antigen complex on the solid support. The antibody-antigen complex on the solid support is washed with water to remove unbound sample and is then treated with anti-TdT. The resulting mixture is then incubated for a period of time sufficient to permit the formation of an antibody-antigen anti-TdT complex on the solid support. The complex on the solid support is washed with water and the amount of anti-TdT bound to the antibody-antigen complex is determined as a measure of the concentration of TdT protein present in the sample.

Solid support refers to an insoluble polymeric material sorptive for TdT antibody. Known materials of this type include hydrocarbon polymers such as polystyrene, polyethylene, polypropylene, polybutylene, butyl rubber and other synthetic rubbers. Other suitable organic polymers include salastic rubber, polyesters, polyamides, cellulose and cellulosic derivatives, acrylate, methacrylates and vinyl chloride and polyvinyl chloride. Copolymers such as graph copolymers of polystyrene are also useful. In addition to the foregoing material the solid support surface may comprise silica gel, silica wafers, glass, insoluble protein metals, and the solid support may be in the form of beads, tubes, strips, discs, and the like.

As used herein the term "anti-TdT" refers to an antibody directed or specific for TdT antigen, and is raised in a nonhuman species such as rabbit, goat, horse, sheep, guinea pig, etc. As previously mentioned, the antibody-antigen complex is reacted with an anti-TdT to form an antibody-antigen-anti-TdT complex in the solid support and the complex is determined as a measure of the concentration of TdT antigen in the sample. The anti-TdT may be directly labeled with a label such as an enzyme or a fluorescent tag, such as a fluorescent dye, to permit determination of the amount bound, or may be indirectly labeled by further reaction, for example, with an antibody specific for anti-TdT which is labeled with an enzyme etc. by conventional methods.

It is preferred to employ direct enzyme labelling of the anti-TdT. Examples of enzymes include catalase, peroxidase, urease, glucose oxidase, phosphatase, and the like. If direct labelling of the anti-TdT is employed, following the formation of the antibody-antigen-TdT* complex, wherein anti-TdT* refers to labeled anti-TdT, an enzyme substrate is added to the ligand and/or solid phase of the reaction mixture and the enzymatic determination is performed utilizing conventional techniques such as colorimetric determinations to measure bound labeled anti-TdT. In the case of indirect labelling, that is, the anti-TdT is unlabelled, the antibody-antigen-anti-TdT complex is washed to remove unbound anti-TdT and subsequently reacted with a labeled antibody to anti-TdT and the bound antibody to anti-TdT is then measured.

The extractant composition utilized in the present invention comprises a nonionic surfactant, anticoagulant, and a reducing agent in a buffered media. Nonionic surfactants useful in the composition of the present invention are well known in the art and include for example, Tween-20, Triton X-100 and the like. It is preferred to employ the nonionic surfactants in the extractant compositions in a concentration of from 0.005%–1% and more preferably, in a range of 0.05%–0.1%. It is most preferred to employ a nonionic surfactant at a concentration of approximately 0.05% in the extraction composition. In addition, it is preferred to employ Tween-20 as the nonionic surfactant. Anticoagulants employed in the extractant compositions are readily ascertained by one of ordinary skill in the art and are employed in a concentration sufficient to prevent coagulation. It is preferred to employ a minimum concentration of anticoagulant of approximately 2.5 mM in the extractant composition. In addition, to increase the stability of the TdT antigen, it is preferred to employ a chelating anticoagulant such as citrates, oxalates, ethylene diaminetetraacetic acid and salts thereof ("EDTA") and the like to stabilize the reducing agent by preventing oxidation of the reducing agent. It is preferred to employ EDTA as the anticoagulant. The term reducing agent refers to a composition which stabilizes TdT by preventing intermolecular disulfide bond formation of the TdT, thus preventing the oxidation of TdT. Such reducing agents are readily ascertained by one of ordinary skill in the art and include thiols such as glutathione and the like. It is preferred to employ glutathione as the reducing agent in the extractant compositions of the present invention. The specific buffered media employed in the extract buffers of the present invention are not critical and is readily ascertained by one of ordinary skill in the art. Any hypotonic buffer may be used and includes for example, phosphate buffered saline, Tris and the like. It is preferred to employ a buffer having a pH range of 5.0 to 8.0 and more preferred to employ a buffer having a pH less than 7.0 and most preferable in a range of 5.5 to 6.5, to minimize auto oxidation of the reducing agent. In addition, to the above components, the extractant composition of the present invention may include a preservative such as thimerosal, to prevent bacterial growth.

As used herein, the term "an effective amount of extractant composition" refers to a quantity of extractant composition sufficient to extract essentially all of the TdT antigen in a sample to be assayed into the buffer supernatant. It is preferred to employ an amount of extractant composition equal to the amount of sample to be extracted.

The following examples illustrate the present invention and are not intended to limit it in spirit or scope,

EXAMPLE 1

EXTRACTION OF TdT ANTIGEN FROM BLOOD EXTRACTS

A blood sample was collected by venipuncture and drawn into a blood collection tube containing ethylene diaminetetraacetic acid. The collected blood sample was frozen at $-20°$ C., and then thawed at room temperature. To a 500 $\mu l$ aliquot of the thawed blood was added 500 $\mu l$ of an extraction buffer containing 0.05% Tween-20, 10 mM EDTA, 20 mM glutathione, 0.01% thimerosal in phosphatase buffered saline (pH 6.0). The resulting extract mixture was stirred and then centrifuged at 200–800 Xg for ten minutes at a temperature of from 2° C. to 8° C. The supernatant containing the TdT antigen was decanted into a clean test tube.

EXAMPLE 2

PREPARATION OF ANTIBODY COATED BEADS

Commercially available goat anti-calf TdT serum was diluted 1:7500 with 0.01M Tris at a pH of 7.5. The diluted solution was used to coat 6 mM polystyrene beads overnight at room temperature and each set of beads was washed and then stored in a solution containing 0.01M tris (pH 7.5) and 0.01M/ml gentamicin, until use.

DETERMINATION OF TdT ANTIGEN

1. A 200 $\mu l$ aliquot of an extracted sample containing TdT antigen obtained from Example 1, and a control specimen were added to appropriate wells of a reaction tray.

2. A polystyrene bead coated with TdT antibody was added to each well containing a sample or control and the reaction trays are covered and incubated for ninety minutes at 30° C. in a water bath.

3. Following the incubation period, unbound sample or control was removed from the wells and the beads were washed three times with water.

4. To the wells containing the washed beads was added 200 $\mu l$ of a solution containing from 0.05–3 $\mu g/ml$ of rabbit anti-TdT covalently linked to horseradish peroxidase in 10% bovine serum in 0.1M Tris and 0.15M sodium chloride.

5. The reaction trays were covered and incubated for ninety minutes at 30° C.

6. Following the incubation, unbound rabbit-anti-TdT-horseradish peroxidase conjugate was removed and the beads were washed three times with water.

7. The beads from the wells originally containing the samples and controls were transferred to assay tubes to which was then added 300 $\mu l$ of a freshly prepared substrate solution containing approximately 27 mg of σ-phenylene diamine.2HCl in 5 ml of citrate-phosphate buffer containing 0.02% hydrogen peroxide at a pH of 5.5. The tubes were then incubated for 30 minutes at room temperature.

8. Following the incubation, 1 ml of 1N sulfuric acid was added to each tube and the absorbance of the resulting sample and control solutions were read on a spectrophotometer at 492 nm.

9. The amount of TdT antigen in the sample is determined by comparing the absorbance obtained from the sample with a standard curve prepared using the above procedure employing known amounts of TdT.

A standard curve is obtained by plotting the absorbance (y-axis) versus the corresponding concentration of the standards (x-axis). The TdT concentration in the specimens, which are run concurrently with the standards, can be determined from the standard curve.

If in an initial assay, a specimen is found to contain an amount of TdT greater than the TdT in the highest standard, the specimen can be diluted with dilution buffer and assayed according to the assay procedure. A 1:10 dilution is recommended using 100 μl of specimen +0.9 ml of dilution buffer.

EXAMPLE 3

Known amounts of purified TdT in the range between 2.5 ng and 25 ng/ml were added to normal human blood and plasma specimens and were assayed in accordance with the procedure described in Example 2. The recovery of TdT was within 95±10%.

EXAMPLE 4

Four lymphocyte extract samples were assayed five times in replicates of three over a five day period in accordance with the peroxidase described in Example 2. The TdT concentration in the specimens were in the range of between 2.5 ng/ml and 25 ng/ml. The intra-assay (within assay) coefficient of variation was between 2.5% and 5.0 % and the inter-assay (between assay) variation between 3.5 and 6.5%.

The TdT standards employed in the above Examples contained TdT in a composition containing 0.025% Tween, 20 mM glutathione and EDTA in a Tris buffer (pH 6.0). For storage stability the TdT standards may be lyophilized.

The sensitivity of the methods of the present invention is approximately 0.4 ng TdT/ml. The sensitivity was calculated as the concentration which is distinguishable from the zero standard, that is, two standard deviations above the zero standard.

Bone marrow and white blood cell samples may be extracted and assayed using a procedure similar to that utilized for whole blood. The use of the extractant composition to extract TdT from bone marrow and white blood cell samples increased the stability of the extracted TdT antigen.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A method for quantitatively determining terminal deoxynucleotidyl transferase (TdT) antigen in a sample comprising:
    (a) extracting the TdT antigen from the sample by treating the sample with an effective amount of an extractant composition comprising a nonionic surfactant, anticoagulant and a reducing agent which stabilizes TdT by preventing intermolecular disulfide bond formation of the TdT and preventing oxidation of TdT in a buffered medium;
    (b) contacting the extracted TdT antigen with a solid support coated with anti-TdT thereby forming an antigen-anti-TdT complex on the solid support;
    (c) treating the antigen-antibody complex on the solid support with a labeled anti-TdT antibody specific for TdT antigen to form an antibody-antigen-anti-TdT complex on the solid support; and
    (d) determining the amount of antibody-antigen-anti-TdT complex formed as a measure of TdT antigen present in the sample.

2. A method according to claim 1 wherein the anticoagulant is a chelating anticoagulant.

3. A method according to claim 2, wherein the chelating anticoagulant is ethylenediaminetetraacetic acid or salts thereof.

4. A method according to claim 1 wherein the reducing agent is glutathione.

5. A method according to claim 1 wherein the nonionic surfactant is TWEEN-20.

6. A method according to claim 1 wherein the extractant composition is buffered at a pH less than 7.

7. A method according to claim 6 wherein the extractant composition is buffered at a pH within a range of 5.5 to 6.5.

8. A method according to claim 7 wherein the extractant comprising TWEEN-20, ethylenediaminetetraacetic acid and glutathione in a phosphate buffered saline medium.

9. A method as in any one of claims 1–8 wherein the anti-TdT is labeled with an enzyme.

10. A method as in any one of claims 1–8 wherein the sample is a blood specimen.

* * * * *